(12) United States Patent
Yoon et al.

(10) Patent No.: US 11,691,032 B2
(45) Date of Patent: Jul. 4, 2023

(54) CARTRIDGE FOR HIGH INTENSITY FOCUSED ULTRASOUND DEVICE COMPRISING PIEZOELECTRIC LINEAR MOTOR AND PIEZOELECTRIC LINEAR MOTOR

(71) Applicant: ECO DM LAB Co., Ltd., Cheongju-si (KR)

(72) Inventors: Man Soon Yoon, Cheongju-si (KR); Young Min Park, Pohang-si (KR); Kyung Sun Lee, Cheongju-si (KR); Myeong Woo Lee, Cheongju-si (KR)

(73) Assignee: ECO DM LAB Co., Ltd.

( * ) Notice: Subject to any disclaimer, the term of this patent is extended or adjusted under 35 U.S.C. 154(b) by 930 days.

(21) Appl. No.: 16/579,804

(22) Filed: Sep. 23, 2019

(65) Prior Publication Data

US 2020/0094082 A1 Mar. 26, 2020

(30) Foreign Application Priority Data

Sep. 21, 2018 (KR) .......................... 10-2018-0113632
Jul. 12, 2019 (KR) .......................... 10-2019-0084415

(51) Int. Cl.
| | |
|---|---|
| *A61N 7/02* | (2006.01) |
| *B06B 1/06* | (2006.01) |
| *H10N 30/87* | (2023.01) |
| *H10N 30/88* | (2023.01) |
| *A61N 7/00* | (2006.01) |

(52) U.S. Cl.
CPC ............... *A61N 7/02* (2013.01); *B06B 1/0651* (2013.01); *H10N 30/875* (2023.02); *H10N 30/877* (2023.02); *H10N 30/883* (2023.02); *A61N 2007/0034* (2013.01); *A61N 2007/0082* (2013.01)

(58) Field of Classification Search
None
See application file for complete search history.

(56) References Cited

U.S. PATENT DOCUMENTS

| 2014/0107542 A1* | 4/2014 | Schubert | ................. A61H 1/00 601/46 |
| 2018/0133470 A1* | 5/2018 | Park | ..................... A61N 5/0616 |

* cited by examiner

*Primary Examiner* — Erica S Lin
(74) *Attorney, Agent, or Firm* — Renaissance IP Law Group LLP

(57) ABSTRACT

A cartridge for a high intensity focused ultrasound (HIFU) device and a piezoelectric linear motor are disclosed. By using the cartridge for a HIFU device according to the present invention, a transducer module is coupled to a piezoelectric linear motor driveable in water and embedded in the cartridge, heat generated when a conventional step motor is driven is fundamentally removed, an additional cooling fan is not needed, ultra-low power consumption and ultra-precise transfer can be realized, and thus an effective procedure can be performed. A skin beauty device may include ultrasound and high frequency units, apply a high frequency to a skin to be treated so as to crack a stratum corneum, and apply ultrasound to the skin to be treated, and thus a medicament drug can easily penetrate the treated skin. In addition, the piezoelectric linear motor in which a piezoelectric actuator and a moving shaft are stably coupled is provided.

7 Claims, 27 Drawing Sheets

CARTRIDGE FOR HIGH INTENSITY FOCUSED ULTRASOUND DEVICE COMPRISING PIEZOELECTRIC LINEAR MOTOR AND PIEZOELECTRIC LINEAR MOTOR

CLAIM FOR PRIORITY

This application claims priority to Korean Patent Application No. 2018-0113632 filed on Sep. 21, 2018 and No. 2019-0084415 filed on Jul. 12, 2019 in the Korean Intellectual Property Office (KIPO), the entire contents of which are hereby incorporated by reference.

BACKGROUND

1. Technical Field

Example embodiments of the present invention relate to the field of ultrasound devices, and more specifically, to a cartridge for a high intensity focused ultrasound device, wherein the cartridge includes a piezoelectric linear motor, and a piezoelectric linear motor providing a stable coupling structure between a piezoelectric actuator and a transfer shaft.

2. Related Art

Ultrasound technologies are widely used in the medical, industry, and environment fields, and as interest in beauty increases recently, various devices using ultrasound to prevent skin aging, reduce wrinkles, or maintain skin elasticity have been introduced.

Ultrasound emitted to a wrinkle area may reduce wrinkles by transferring heat to a superficial muscular aponeurotic system (SMAS), which is a root cause of the wrinkles, and shrinking or coagulating skin tissues using the transferred heat. Since skin care devices use this principle, devices which may improve efficiency by focusing ultrasound only on a specific area to be treated are commercially available. Recently, an ultrasound device using a high intensity focused ultrasound (HIFU) is non-invasively used for a medical or aesthetic purpose.

As illustrated in FIG. 1, an ultrasound device generating such a HIFU includes a cartridge 1 having a transducer and a handpiece (main body) 2 coupled to the cartridge. The cartridge is replaceable and is filled with an acoustic liquid such as water.

FIGS. 2A to 2C are views illustrating an internal structure of a cartridge conventionally used in a HIFU device.

FIG. 2A shows an overall internal structure of the conventional cartridge for a HIFU device, FIG. 2B shows an upper structure of the conventional cartridge, and FIG. 2C shows one side surface of the conventional cartridge. Referring to FIGS. 2A to 2C, the conventional cartridge for a HIFU device is surrounded by a cartridge housing 10, and a transmission window 11 to which an ultrasound transmission film for transferring ultrasound energy to a skin when in contact with the skin is formed in a lower portion of the cartridge housing 10. In the cartridge, a HIFU generating transducer 12 is fixed to a support 13 in the cartridge, and the support 13 is connected to a transfer shaft 14 to move laterally. The transfer shaft 14 is surrounded by a rubber bellows 15 to prevent contact with water, and the rubber bellows 15 is bonded to both end portion of the outer case 10 using an adhesive so as to prevent leakage. In addition, metal guide fins 16 are installed on side surfaces of the support 13 to control a sway phenomenon in left and right directions when the support 13 supporting the transducer 12 is moved in the cartridge by a direct current (DC) motor installed at the outside.

In addition, as illustrated in FIG. 2C, a connector 17 coupled to a step motor is formed on one outer surface of the cartridge.

FIGS. 3A, 3B, and 3C are schematic views illustrating components of the HIFU generating transducer used in the cartridge for a HIFU device.

As illustrated in FIGS. 3A, 3B, and 3C, the transducer includes a dome type HIFU piezoelectric element (see FIG. 3A), a piezoelectric element housing (see FIG. 3B), a printed circuit board (PCB) (see FIG. 3C), and wires.

Specifically, FIG. 3A shows a general HIFU piezoelectric element. Ag electrodes 21a and 21b for applying electricity to a dome type piezoelectric actuator 20 which generates HIFU are formed on front and rear surfaces of the HIFU piezoelectric element, and wires 22 are soldered to the Ag electrodes 21a and 21b.

Generally, the HIFU piezoelectric element, as an element using an optical principle, is typically machined in a spherical lens form and used. Generally, a focal distance of light passing through a spherical lens varies according to wavelengths, and the focal distance decreases as the wavelength becomes longer. Due to such an optical principle, when a voltage is applied to the HIFU piezoelectric element, ultrasound energy generated during a thickness mode vibration is focused on a center of a radius of curvature, and ultrasound vibrations are accumulated.

The HIFU piezoelectric element 20 configured as described above is seated in a plastic housing 23 to be separated from water in a cartridge container.

FIG. 3B shows a structure of the housing 23 of the piezoelectric element. As illustrated in FIG. 3B, steps are installed on lower and upper end portions of an inner wall of the housing 23, the piezoelectric element 20 is bonded to and seated on a lower end step 24 using an epoxy, and a PCB (see FIG. 3C) is seated on an upper end step 24'.

FIG. 3C shows the PCB used in the transducer. As illustrated in FIG. 3C, PCB holes 25 are formed in the PCB such that the wires bonded to the piezoelectric element pass through the PCB and are withdrawn to the outside when being coupled to the piezoelectric element.

Manufacturing of the transducer will be described below.

The HIFU piezoelectric element is seated on the lower end step 24 of the housing 23 using the epoxy. Then, the PCB is seated on the upper end step 24' of the housing 23 using the epoxy. Next, after the wires 22 of the HIFU piezoelectric element are withdrawn to the outside through the PCB holes 25, the wires 22 are connected to wires 26, which are covered by insulating sheaths and are connected to a circuit through the PCB holes 25, through soldering. Finally, the PCB is coated with a liquid silicone 27 for waterproofing and insulation and is cured to manufacture the transducer. A final form of the manufactured transducer is illustrated in FIG. 3D.

The transducer 12 manufactured as described above is coupled to the support 13 and installed in the cartridge container.

FIG. 4 shows an ultrasound transmission film 30 to be attached to an open portion for the cartridge for a HIFU device. The polymer film is attached to the open portion of the cartridge so as to minimize attenuation of focused ultrasound energy to transmit the ultrasound energy emitted from the transducer to the skin and to prevent water in a container from leaking. An adhesive member 31 is formed on an edge of the ultrasound transmission film 30 such that the ultrasound transmission film 30 is attached to the open portion of the cartridge.

Water, which is a sound wave transmission medium, and the transducer are accommodated in the conventional cartridge for a HIFU device, and a step motor is installed outside the conventional cartridge for a HIFU device so as to precisely move the transducer. However, since heat is generated when the step motor is driven, a cooling fan should be used as a subsidiary device, and thus there are problems in that volume is increased and power consumption is also increased.

Accordingly, a new cartridge for a HIFU device having decreased volume and a power saving effect is needed.

Meanwhile, a piezoelectric motor is a next generation motor using a piezoelectric effect of a piezoelectric ceramic which vibrates according to a change in applied electric field. The piezoelectric motor is a noiseless motor and is also referred to as an ultrasound motor having a driving frequency in an ultrasound band greater than 20 kHz or more which may not be detected by human ears.

Although a vibration transmission method of the conventional piezoelectric motor is a traveling or standing wave method, the vibration transmission method causes abrasion at contact portions due to repeated driving. Due to the abrasion at the contact portions, there is a problem in that it is difficult to obtain a constant amplitude. In order to solve such a disadvantage of the vibration transmission method, a piezoelectric linear motor which moves a moving body has been developed. An early piezoelectric linear motor has a structure in which a piezoelectric ceramic is coupled to a moving shaft on which a moving body mounted. In the early piezoelectric linear motor, since the piezoelectric ceramic is a flat type, an elastic plate should be coupled to the piezoelectric ceramic so as to obtain displacement. Such a structure and a manufacturing process cause an increase in cost and complexity in the manufacturing process.

The inventor of the present invention proposed a piezoelectric linear motor including a dome type actuator in Korean Patent Registration No. 10-0768513.

FIGS. 19 and 20 are views illustrating a conventional dome type piezoelectric linear motor.

As illustrated in FIGS. 19 and 20, in the conventional piezoelectric linear motor including a dome type piezoelectric actuator, a moving shaft 7 is bonded to a peak of a dome type piezoelectric actuator 6 using an epoxy. The drawing symbol "8" denotes a support ceramic.

In the conventional dome type piezoelectric linear motor, the peak of the dome type actuator 6 is inevitably in point contact with a carbon rod which is the moving shaft 7 at a bonding portion. Accordingly, the bonding portion of the peak of the dome type piezoelectric actuator 6 and the moving shaft 7 is weak. Since vibration of the piezoelectric dome type actuator 6 is transmitted to the carbon rod which is a moving shaft, there is a possibility in that cracks may occur at a contact point of the carbon rod and the dome type piezoelectric actuator 6. In this case, heat is generated due to vibration energy, the epoxy is melted as described in FIG. 2, and thus the moving shaft 7 is frequently separated from the dome type piezoelectric actuator 6.

SUMMARY

Accordingly, example embodiments of the present invention are provided to substantially obviate one or more problems due to limitations and disadvantages of the related art.

Example embodiments of the present invention provide a cartridge for a high intensity focused ultrasound (HIFU) device in which a piezoelectric linear motor capable of being driven in water is embedded.

Example embodiments of the present invention also provide a HIFU device including the cartridge and a handpiece coupled to the cartridge.

Example embodiments of the present invention also provide a piezoelectric linear motor capable of having a stable boning structure between a dome type piezoelectric actuator and a moving shaft.

However, objectives to be solved by the present invention are not limited to the above described objectives, and other objectives which are not described above will be clearly understood by those skilled in the art through the following specification.

In some example embodiments, a cartridge for a high intensity focused ultrasound device includes a cartridge housing in which a sound transmission medium is stored and a transmission window sealed by an ultrasound transmission film is formed in a lower portion thereof, a transducer embedded in the cartridge housing, controlled by a main body, and configured to generate a high intensity focused ultrasound, and a piezoelectric linear motor embedded in the cartridge housing, controlled by the main body, and configured to transfer the transducer.

The transducer may include a transducer housing, a dome type piezoelectric actuator installed on a lower end portion of the transducer housing and configured to generate high intensity focused ultrasound, silver electrodes applied on an upper surface and a lower surface of the piezoelectric actuator, and wires connected to the silver electrodes, wherein the transducer may be embedded in a support to be transferred.

The piezoelectric linear motor may include a dome type piezoelectric actuator, a transfer shaft that is disposed at and perpendicular to a center of a convex surface of the piezoelectric actuator and formed to have a predetermined length, a connector connecting the piezoelectric actuator and the transfer shaft, silver electrodes applied on an upper surface and a lower surface of the piezoelectric actuator, and wires connected to the silver electrodes, wherein the piezoelectric actuator may be covered by a housing for waterproofing.

The transducer and the piezoelectric linear motor may be detachably coupled to the cartridge housing using a bolt or a coupling method.

The transducer may be coupled and integrated with a transfer shaft of the piezoelectric linear motor using a support.

The transducer may be integrally coupled to the piezoelectric linear motor by inserting a transfer member into an inner space of the support of the transducer, and passing the transfer shaft of the piezoelectric linear motor through the transfer member and a hole of the support.

In other example embodiments, a high intensity focused ultrasound device includes a cartridge including a transducer and a piezoelectric linear motor, and a main body coupled to the cartridge, wherein the main body includes a circuit and a power source, and the circuit is connected to the transducer and the piezoelectric linear motor of the cartridge through wires.

Wiring of the transducer and the piezoelectric linear motor to the circuit may be performed by connecting the wire, which is formed in an upper portion of a piezoelectric actuator of the piezoelectric linear motor connected to a transfer shaft in contact with a medium in the cartridge, and the wire formed in a lower portion of a piezoelectric actuator of the transducer to a common ground terminal of the circuit and connecting the remaining wire to a power terminal of the circuit.

In still other example embodiments, a piezoelectric linear motor includes a dome type piezoelectric actuator, a moving shaft coupled to the piezoelectric actuator, and a moving member mounted on the moving shaft, wherein a protrusion is formed in a peak portion of the piezoelectric actuator.

An end portion of the moving shaft may be in direct contact with the protrusion or be in indirect contact with the protrusion with a coupler interposed therebetween.

A planar cross section of the protrusion may have a circular or polygonal shape.

The coupler may include a first groove and a second groove into which the protrusion and the moving shaft are respectively inserted from both sides of the coupler.

The coupler may have an electrical conductivity of $10^5$ S/m or more.

A material of the coupler may be aluminum, copper, titanium, nickel, tungsten, stainless steel, or an alloy thereof.

The first groove and the second groove may be coaxially disposed.

The first groove may communicate with the second groove.

The first groove may not communicate with the second groove, and bottom surfaces of the first groove and the second groove may be flat surfaces.

An epoxy may be used to bond the piezoelectric actuator to the coupler and to bond the coupler to the moving shaft.

A difference between a curvature of a coupler portion in contact with a curved surface of the piezoelectric actuator and a curvature of the piezoelectric actuator may be less than 10%.

The coupler portion in contact with the piezoelectric actuator may have a curvature ranging from 2 mm to 20 mm.

The epoxy may include a metal powder.

Another example of the coupler may include a cylindrical ceramic having a vertically open hole, and a density of the cylindrical ceramic coupler may be between a density of the piezoelectric actuator and a density of the moving shaft.

BRIEF DESCRIPTION OF DRAWINGS

Example embodiments of the present invention will become more apparent by describing example embodiments of the present invention in detail with reference to the accompanying drawings, in which:

FIG. 23A is a cross-sectional view illustrating the dome type piezoelectric actuator, FIG. 23B is a perspective view illustrating the dome type piezoelectric actuator, and FIG. 23C is a front view illustrating the dome type piezoelectric actuator;

DESCRIPTION OF EXAMPLE EMBODIMENTS

Hereinafter, embodiments of the present invention will be described in detail with reference to the accompanying drawings. However, the embodiments described below may be variously changed. The embodiments described below are not intended to limit the present invention to the embodiments, and it is to be appreciated that all changes, equivalents, and substitutes thereof are encompassed in the present invention.

The terminology used for describing the embodiment is to describe the embodiments of the present invention but is not intended to limit the scope of the present invention. The use of the singular form in the present document does not preclude the presence of more than one referent unless the context clearly indicates otherwise. It should be understood that the terms "comprise," "comprising," "include," and/or "including," when used herein, specify the presence of stated features, numbers, steps, operations, elements, and/or components, but do not preclude the presence or addition of one or more other features, numbers, steps, operations, elements, components, and/or groups thereof.

Unless otherwise defined, all terms (including technical and scientific terms) used herein are to be interpreted as is customary in the art to which this invention belongs. It should be further understood that terms in common usage should also be interpreted as is customary in the relevant art and not in an idealized or overly formal sense unless expressly so defined herein.

The present invention provides a cartridge for a high intensity focused ultrasound (HIFU) device in which a piezoelectric linear motor is embedded.

Hereinafter, the cartridge according to the present invention will be described in detail with reference to the accompanying drawings.

Figure 1:
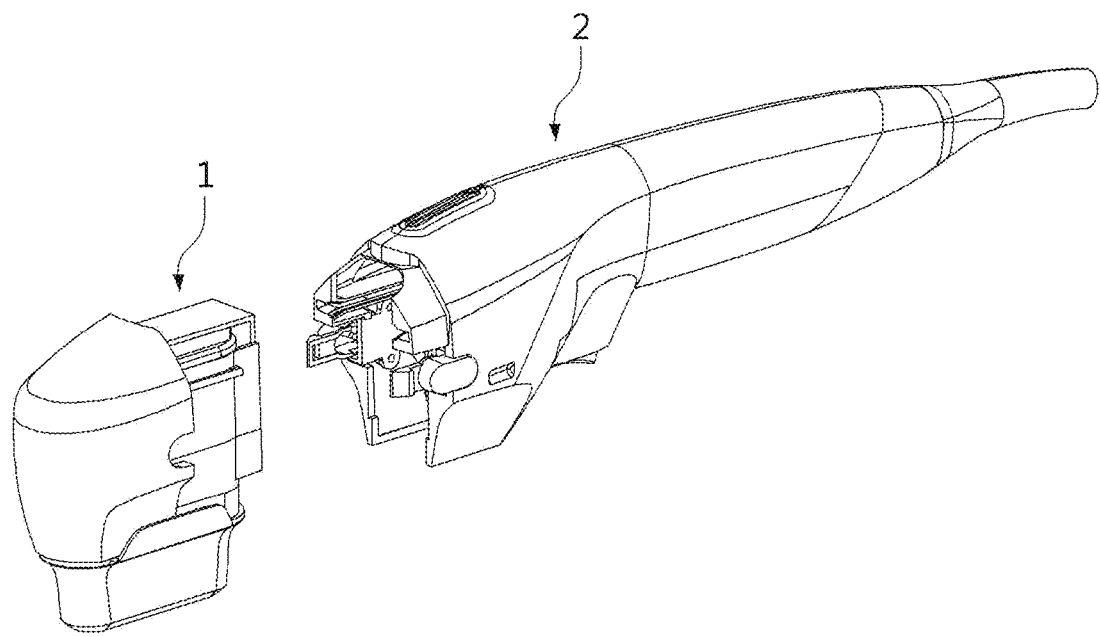
FIG. 1 is a schematic view illustrating a general high intensity focused ultrasound (HIFU) device.
Figure 2A:
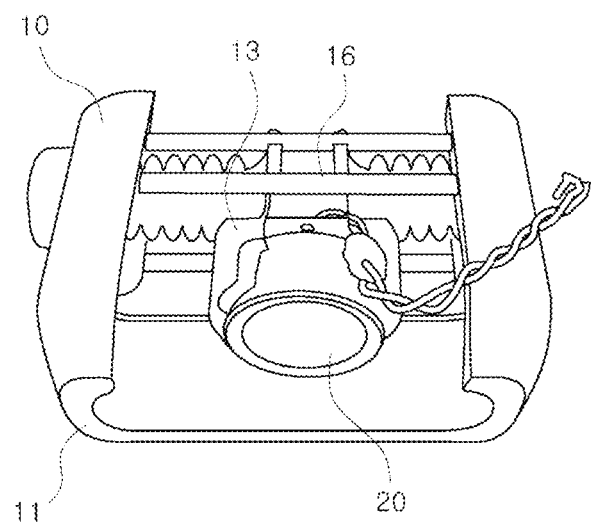
FIG. 2A to 2C are schematic views illustrating an internal structure of a conventional cartridge for a HIFU device (FIG. 2A is a front view illustrating an interior of the cartridge, FIG. 2B is a plan view illustrating the interior of the cartridge, and FIG. 2C is a side perspective view illustrating the cartridge)
Figure 2B:
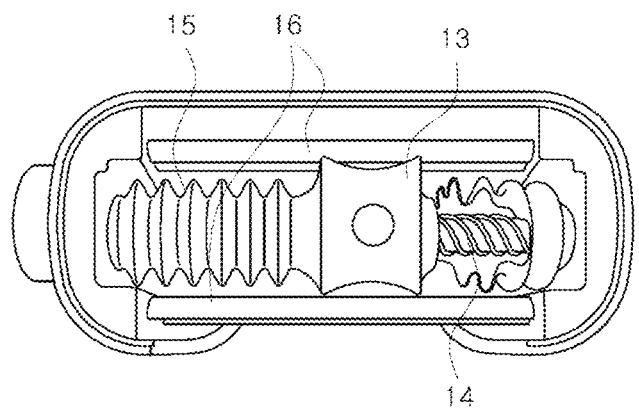
Figure 2C:
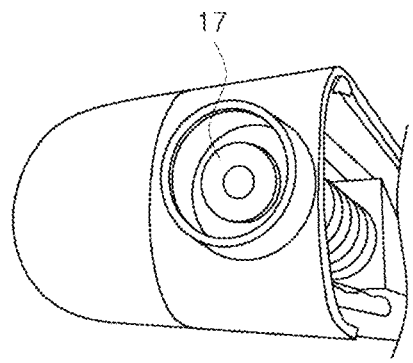
Figure 3A:
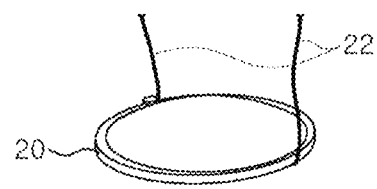
FIGS. 3A to 3E are views illustrating components, which are used in the conventional cartridge for a HIFU device, of the general HIFU transducer.
Figure 3B:
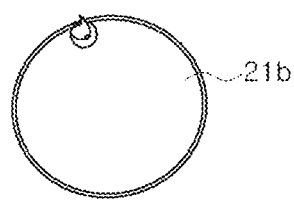
Figure 3C:
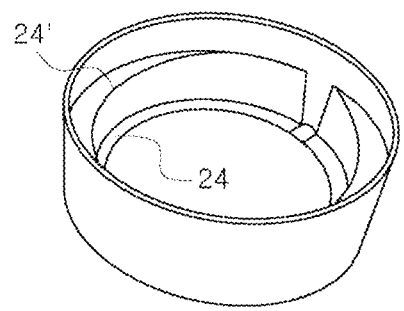
Figure 3D:
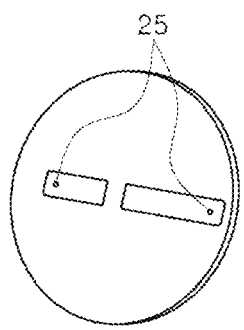
Figure 3E:
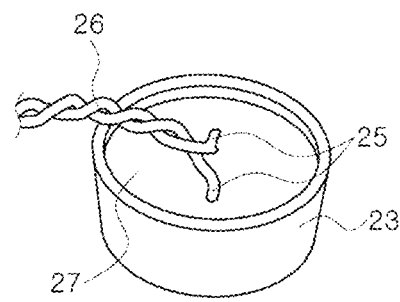
Figure 4:
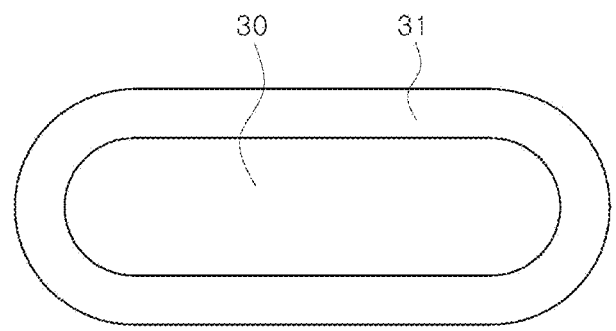
FIG. 4 is a view illustrating a general ultrasound transmission film used in the conventional cartridge for a HIFU device.
Figure 5A:
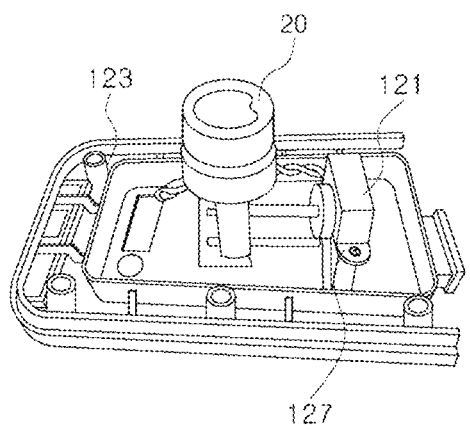
FIGS. 5A and 5B are views illustrating an internal structure of a cartridge for a HIFU device according to one embodiment of the present invention (FIG. 5A is a view illustrating an upper plate structure and FIG. 5B is a view illustrating a lower plate structure)
Figure 5B:
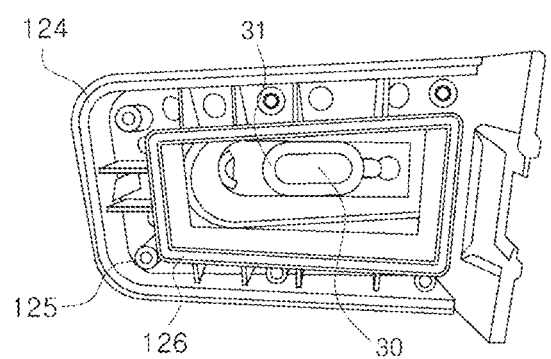

FIGS. 5A and 5B are views illustrating an internal structure of a cartridge for a HIFU device according to one embodiment of the present invention (FIG. 5A is a view illustrating an upper plate structure and FIG. 5B is a view illustrating a lower plate structure);

Referring to FIGS. 5A and 5B, the cartridge for a HIFU device according to one embodiment of the present invention is provided with an upper plate of FIG. 5A and a lower plate of FIG. 5B and includes a cartridge housing which stores a sound transmission medium therein and in which a transmission window sealed by an ultrasound transmission film is formed in a lower portion thereof, a HIFU generating transducer provided in the cartridge housing, and a piezoelectric linear motor.

FIG. 5A shows the upper plate structure of the cartridge for a HIFU device according to the present invention.

A feature of the present invention is that both of the HIFU generating transducer and the piezoelectric linear motor for transferring the transducer are provided in the cartridge. Since the piezoelectric linear motor may be driven in water even with a power consumption of one watt or less, ultra-low power consumption can be realized. In addition, since the piezoelectric linear motor may constantly transfer ultrasound less than 1 mm which is effective in skin regeneration, ultra-precise transfer may be performed.

The transducer is coupled to a transfer shaft of the piezoelectric linear motor, formed in an integral form, and coupled to an upper plate. In this case, the transducer and a piezoelectric element in the piezoelectric linear motor may preferably be surrounded by a plastic housing so as to be separated from water in the cartridge.

The transducer may be a generally used transducer in the art.

As illustrated in FIG. 3, the transducer may include a transducer housing, a dome type piezoelectric actuator which is installed on an end portion of the transducer housing and generates a high intensity focused ultrasound, silver electrodes applied on upper and lower surface of the piezoelectric actuator, and wires connected to the silver electrodes and may be embedded in a support so as to be transferred. Since the detailed contents are the same as the descriptions of FIG. 3, the detailed contents will be omitted.

The piezoelectric linear motor will be described in detail with reference to FIG. 6 below.

In the cartridge according to the present invention, the transducer and the piezoelectric linear motor are detachably coupled to the upper plate using bolts. Accordingly, in a case in which the transducer and the piezoelectric linear motor are individually damaged or broken and need to be replaced, the transducer and the piezoelectric linear motor may be easily replaced and used by being detached from and attached to the upper plate.

FIG. 5B shows the lower plate structure of the cartridge according to the present invention for a HIFU device.

A sound transmission medium, preferably water, may be stored in the lower plate, and the transmission window for effectively transferring ultrasound energy of the HIFU to the skin is formed in the lower plate, and the lower plate includes an ultrasound transmission film attached to the transmission window. In this case, a polymer film generally used in the art may be used as the ultrasound transmission film. An adhesive portion is formed in an edge of the ultrasound transmission film such that the ultrasound transmission film is attached to the transmission window.

Figure 15:
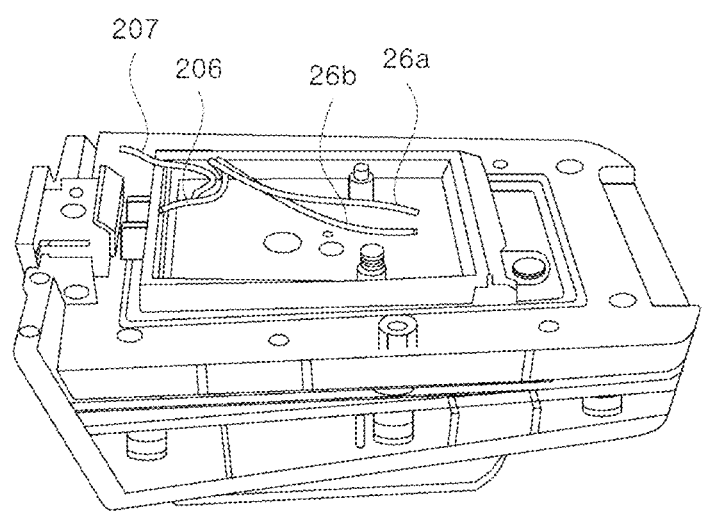
FIG. 15 is a view illustrating a form in which an upper plate and a lower plate of the cartridge for a HIFU device according to one embodiment of the present invention are coupled.

The upper plate and the lower plate of the cartridge according to the present invention may be coupled using nuts and bolts. A sealing rubber packing is inserted between the upper plate and the lower plate to prevent water leakage. A coupling state of the cartridge according to the present invention is illustrated in FIG. 15.

Figure 6A:
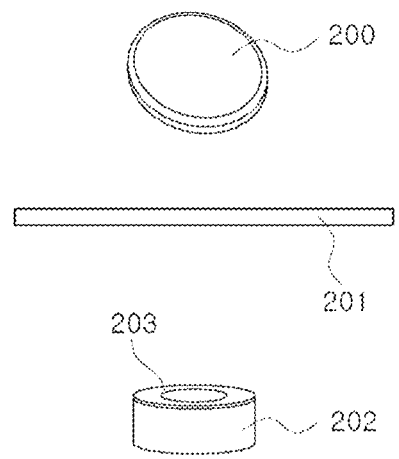
FIGS. 6A to 6C are views illustrating components of a piezoelectric linear motor used in the cartridge for a HIFU device according to one embodiment of the present invention.
Figure 6B:
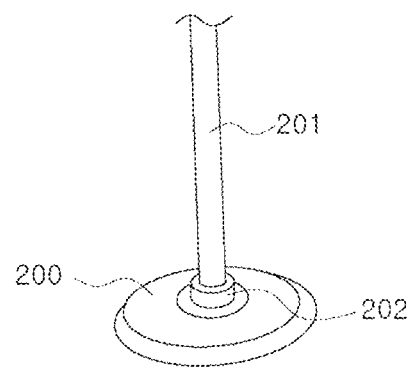
Figure 6C:
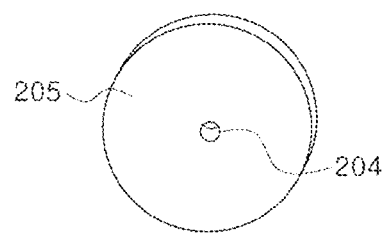

FIGS. 6A to 6C are views illustrating components of the piezoelectric linear motor used in the cartridge for a HIFU device according to one embodiment of the present invention.

FIG. 6A shows the components of the piezoelectric linear motor. As illustrated in FIG. 6A, the piezoelectric linear motor includes a dome type piezoelectric actuator 200 which generates large displacement, a transfer shaft 201 which transfers the generated displacement as a transfer force, and a connector 202 connecting the piezoelectric actuator and the transfer shaft. As illustrated in FIG. 6B, first, the connector 202 having a ring type is attached to a center of a convex surface of the dome type piezoelectric actuator 200 using an epoxy, and a carbon rod 201 serving as a transfer shaft is connected to a hole 203 formed at a center of the connector using an adhesive in the piezoelectric linear motor. Front and rear surfaces of the dome type piezoelectric actuator 200 are coated with silver (Ag) electrodes 200a and

200b to apply electricity, and the silver electrodes 200a and 200b are soldered to upper and lower wires so as to apply an electric signal.

In addition, in order to apply a mass to the piezoelectric linear motor to increase a forward force of the linear motor and to insulate the upper and lower silver electrodes when the piezoelectric linear motor is in contact with the sound transmission medium (water), a lower ceramic 205 (see FIG. 6C), in which a hole 204 having a size equal to a thickness of the wire is formed at a center thereof, may be coupled to a lower portion of the piezoelectric actuator. In this case, the lower wire is guided to the outside through the hole of the lower ceramic.

The piezoelectric linear motor manufactured through the above method is illustrated in FIG. 7.

Figure 7A:
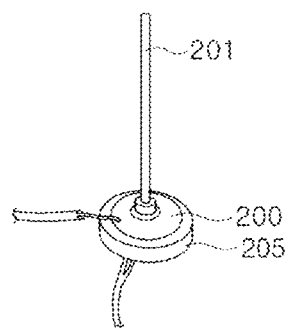
FIGS. 7A and 7B are views illustrating the form of a final structure manufactured with the components of the piezoelectric linear motor according to one embodiment of the present invention (FIG. 7A is a side view illustrating the form and FIG. 7B is a bottom view illustrating the form)
Figure 7B:
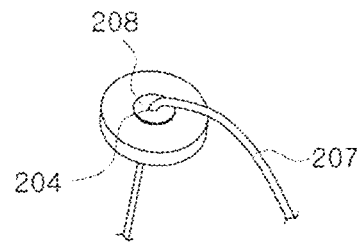

FIGS. 7A and 7B are views illustrating the form of a final structure manufactured with the components of the piezoelectric linear motor according to one embodiment of the present invention. In this case, FIG. 7A is a side view illustrating the form, and FIG. 7B is a bottom view illustrating the form.

As illustrated in FIG. 7B, a lower wire 207 connected to a lower electrode of the piezoelectric actuator 200 of the piezoelectric linear motor is guided to the outside through the hole 204 of the lower ceramic 205, and a treatment for preventing water leakage may be performed between the hole 204 of the lower ceramic and the wire using a silicone adhesive.

Figure 8A:
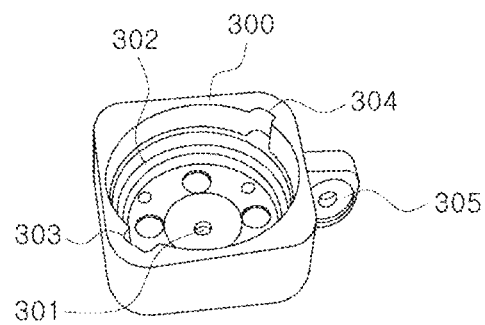
FIGS. 8A and 8B are views illustrating a structure of a piezoelectric linear motor housing used in the cartridge for a HIFU device according to one embodiment of the present invention.
Figure 8B:
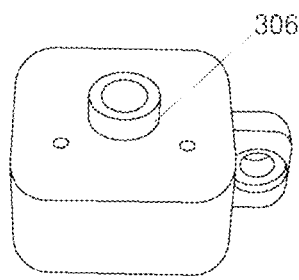

FIGS. 8A and 8B are views illustrating a structure of a piezoelectric linear motor housing used in the cartridge for a HIFU device according to one embodiment of the present invention.

Specifically, FIGS. 8A and 8B include a rear view of FIG. 8A and a front view of FIG. 8B which illustrate a structure of a housing of the piezoelectric actuator for separating the piezoelectric actuator which is a vibration generator of the piezoelectric linear motor from a sound liquid. As illustrated in FIG. 8A, in a lower end portion of the housing of the piezoelectric actuator, a step 302 on which the piezoelectric actuator is seated, and a groove 303, through which the wires connected to the upper electrode and the lower electrode of the piezoelectric actuator are guided, and a groove 304 for assembly of the cover are formed to face each other. A hole 301 through which the carbon rod which is the transfer shaft may pass is formed at a center of an upper end portion of the housing, and as illustrated in the FIG. 8B, a protrusion 306 is formed at the hole through which the carbon rod passes. In addition, in the piezoelectric linear motor housing 300, a protrusion 305 through which a bolt may be inserted into the outside of the housing may be formed to install the piezoelectric linear motor on the upper plate of the cartridge.

Figure 9:
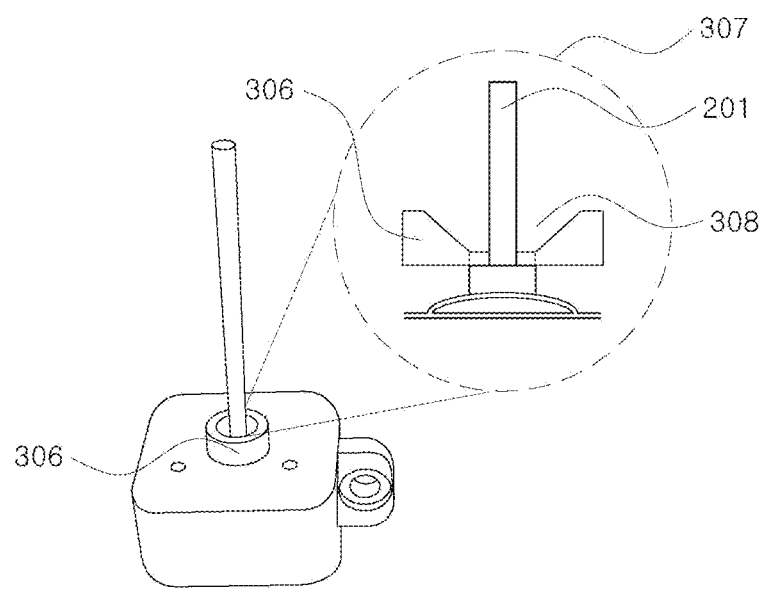
FIG. 9 is a view illustrating a form in which the piezoelectric linear motor is coupled into the piezoelectric linear motor housing used in the cartridge for a HIFU device according to one embodiment of the present invention.

FIG. 9 is a view illustrating a form in which the piezoelectric linear motor is coupled into the piezoelectric linear motor housing.

In this case, in FIG. 9, the enlarged protrusion 306 at a center of a housing cover through which the transfer shaft passes is illustrated in a dotted circle 307. Specifically, an interior of the protrusion of an upper portion of the housing may be preferably formed to have an inclined surface so as to easily perform silicon coating 308 for waterproofing between the carbon shaft and an inner space of the housing after the carbon shaft 201 passes through the hole of the housing and is installed.

Figure 10A:
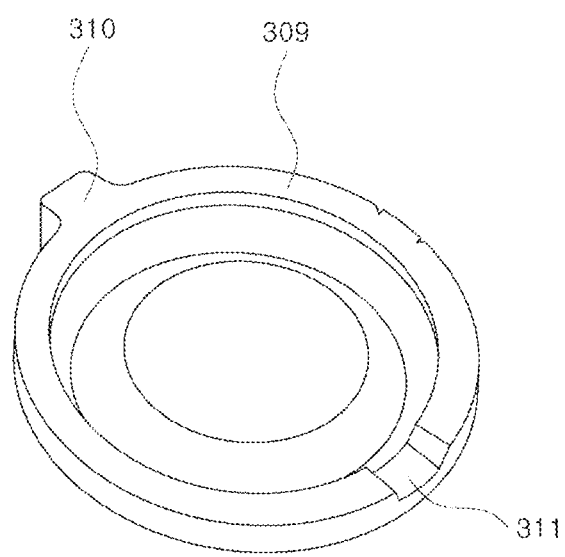
FIGS. 10A and 10B are views illustrating a cover which covers the piezoelectric linear motor housing used in the cartridge for a HIFU device according to one embodiment of the present invention.
Figure 10B:
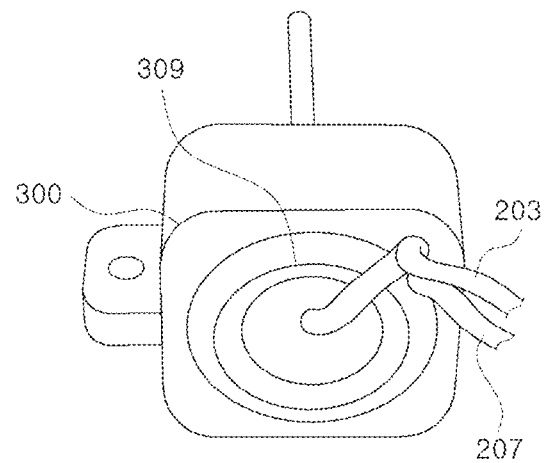

FIGS. 10A and 10B are views illustrating a cover which covers the piezoelectric linear motor housing.

After the piezoelectric actuator of the piezoelectric linear motor is seated on the housing, the cover 309 which covers the housing may be used for waterproofing. The housing cover is illustrated in FIG. 10A.

In this case, a protrusion 310 of one side of the cover is inserted into the groove 303 of the housing, the protrusion 310 is finished using a silicone adhesive after the wire is guided to the outside through a groove 311 formed to face the groove 303, and thus the piezoelectric actuator is prevented from being in contact with water in the cartridge due to the housing. A form in which the piezoelectric linear motor is coupled into the piezoelectric linear motor housing and the piezoelectric linear motor housing is covered by the cover is illustrated in FIG. 10B.

FIGS. 11A to 11D are views illustrating a structure of a transfer member used in the cartridge for a HIFU device according to one embodiment of the present invention.

Figure 11A:
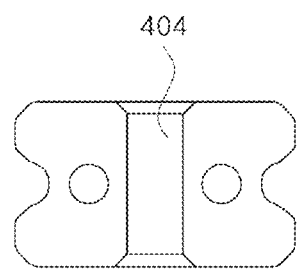
FIGS. 11A to 11D are views illustrating a structure of a transfer member used in the cartridge for a HIFU device according to one embodiment of the present invention.
Figure 11B:
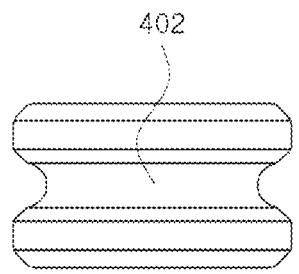
Figure 11C:
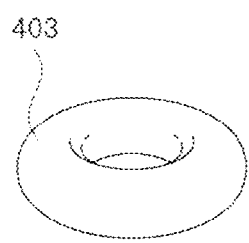
Figure 11D:
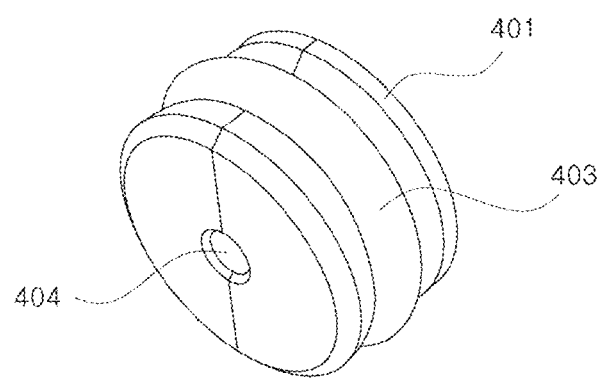

In the cartridge according to the present invention, the transfer member is formed around the carbon shaft of the piezoelectric linear motor. The transfer member is coupled to the transducer to serve to transfer the transducer. As illustrated in FIG. 11A, the transfer member is provided with two stainless pieces 401 and a groove 404 having an inner diameter equal to a diameter of the carbon shaft is formed at a center of one side of the transfer member. A form in which the two pieces of the transfer member are coupled is illustrated in FIG. 11B. A groove 402 is formed in a side surface of a transfer member coupled body of the two coupled pieces, and a silicone ring 403 illustrated in FIG. 11C is installed in the groove. A final form of the transfer member assembled as described above is illustrated in FIG. 11D.

Figure 12:
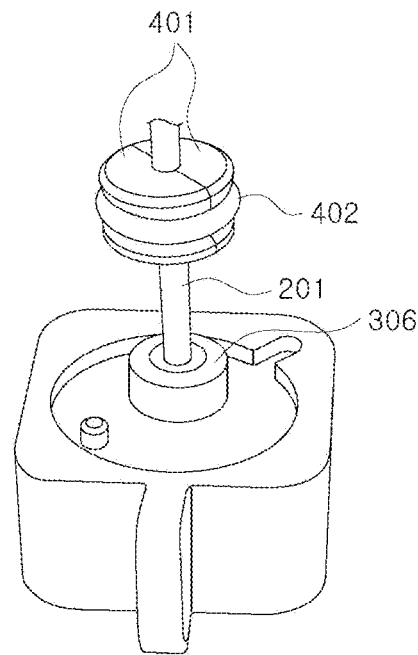
FIG. 12 is a view illustrating a form in which the housing and the transfer member are coupled to the piezoelectric linear motor used in the cartridge for a HIFU device according to one embodiment of the present invention.

FIG. 12 is a view illustrating a form in which the housing and the transfer member are coupled to the piezoelectric linear motor used in the cartridge for a HIFU device according to one embodiment of the present invention.

As illustrated in FIG. 12, the transfer member is coupled to a part of the carbon shaft of the piezoelectric linear motor. Then, the support which fixes the transducer is coupled to the transfer member, the support coupled to the transfer member moves according to moving of the transfer member, and as a result, the transducer fixed to the support is transferred to transfer HIFU to a desired position.

Figure 13A:
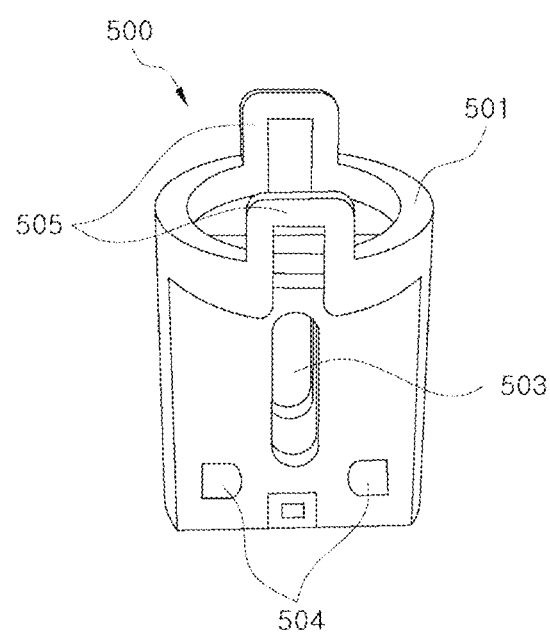
FIGS. 13A and 13B are views illustrating a structure of a transducer support used in the cartridge for a HIFU device according to one embodiment of the present invention.
Figure 13B:
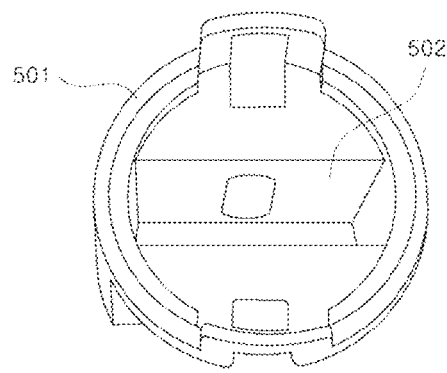

FIGS. 13A and 13B are views illustrating a structure of a transducer support 500 used in the cartridge for a HIFU device according to one embodiment of the present invention.

FIG. 13A is a front view illustrating the transducer support, and FIG. 13B is a plan view illustrating the transducer support.

The support 500 may serve to fix a HIFU transducer and be coupled to the transfer member of the piezoelectric linear motor to move the HIFU transducer.

Referring to FIGS. 13A and 13B, in the support 500, an inner space 502, into which the transfer member is inserted so that the support 500 is integrated with the transfer member installed in the carbon shaft of the piezoelectric linear motor as a single coupled body and moves, and holes 503, through which the shaft may pass, are formed in both sides thereof, and in order to prevent shaking of the transfer shaft, two holes 504 through which guide fins pass are formed in a lower end portion of the support. In addition, HIFU transducer installation portions 505 having hook forms are disposed on an upper end portion of the support to install the HIFU transducer.

Figure 14A:
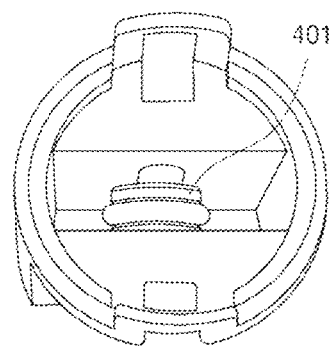
FIGS. 14A and 14B are views illustrating a form in which a piezoelectric linear motor module is coupled to the transducer support in the cartridge for a HIFU device according to one embodiment of the present invention.
Figure 14B:
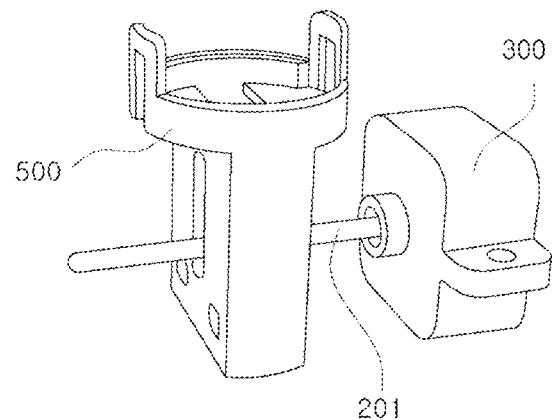

FIGS. 14A and 14B are views illustrating a form in which a piezoelectric linear motor module is coupled to the transducer support in the cartridge for a HIFU device according to one embodiment of the present invention.

Specifically, FIG. 14A is a plan view illustrating the form in which the transfer member is inserted into the transducer support, and FIG. 14B is a perspective view illustrating a form in which the coupled body into which the transfer member is inserted is coupled to the carbon shaft of the piezoelectric linear motor in the transducer support.

A coupling method of the piezoelectric linear motor and the transducer support will be described below.

First, as illustrated in FIG. 14A, the transfer member 401 is inserted into the inner space of the support. Then, the transfer shaft 201 of the piezoelectric linear motor may pass through the hole formed at the center of the transfer member and the holes formed in the side surfaces of the support to couple the support 500 and the piezoelectric linear motor. The form in which the support is coupled to the transfer shaft of the piezoelectric linear motor is illustrated in FIG. 14B.

Then, the transducer may be installed in the installation portions of the upper end portion of the support.

A coupled body, which is formed through above described method, of the transducer and the piezoelectric linear motor is installed on the upper plate of the cartridge according to the present invention, and the ultrasound transmission film is attached to the transmission window of the lower plate of the cartridge. In addition, in order to prevent shaking of the transfer shaft, the guide fins (not shown) pass through the holes of the lower end portion of the support to fix the support to the cartridge upper plate.

Then, the cartridge according to the present invention may be manufactured by assembling the upper plate with the lower plate. A form of the manufactured cartridge is illustrated in FIG. 15.

As illustrated in FIG. 15, in the cartridge according to the present invention, wires 206, 207, 26a, and 26b which are wired therein to drive the piezoelectric linear motor and the transducer are withdrawn through the hole formed in the upper plate, and a gap of the hole is sealed using a silicone.

In addition, the present invention provides a HIFU device including the HIFU cartridge.

Figure 16:
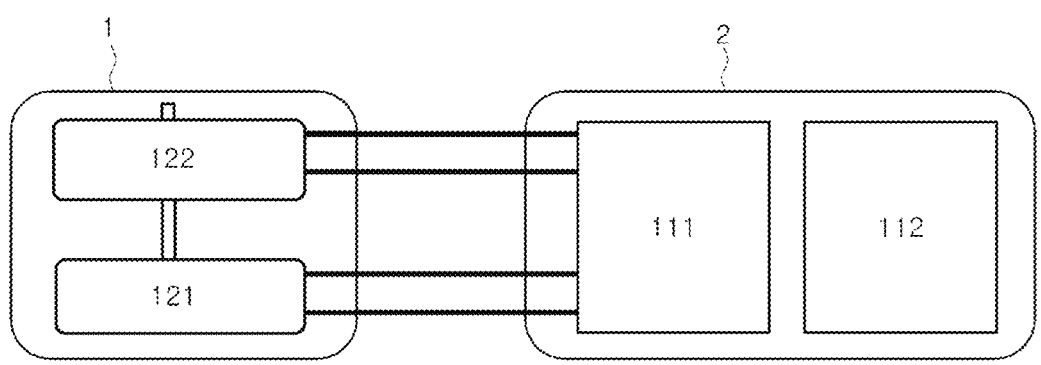
FIG. 16 is a schematic view illustrating a HIFU device according to one embodiment of the present invention.

FIG. 16 is a schematic view illustrating the HIFU device according to one embodiment of the present invention.

Referring to FIG. 16, the HIFU device according to the present invention is provided with a cartridge 1 in direct contact with skin and a main body 2 coupled to the cartridge 1.

In the cartridge 1, a HIFU transducer 122 and a piezoelectric linear motor 121 are integrally coupled and provided, and in the main body 2, a circuit 111 and a power source 112 are provided. The circuit 111 is electrically connected to the HIFU transducer 122 and the piezoelectric linear motor 121 of the cartridge.

Since the detailed description about the cartridge is the same as the above description, the detailed description about the cartridge will be omitted to avoid the repeated description.

The circuit 111 is disposed to be electrically connected to the HIFU transducer 122 and the piezoelectric linear motor 121 of the cartridge to serve to apply a voltage to the HIFU transducer and the piezoelectric linear motor so as to drive the HIFU transducer and the piezoelectric linear motor. In this case, any type of a circuit disposed in a general device may be applied to the circuit 111, and the present invention is not particularly limited thereto.

The power source 112 is electrically connected to the circuit 111 using a wire to serve to provide power to the circuit 111. The external power source 112 may be an external battery, a wireless battery, or an alternating current power source.

A method of driving the HIFU device according to the present invention will be described below.

First, when power is supplied through the power source after the HIFU cartridge according to the present invention is connected to a circuit of a handpiece, since a current flows through the circuit electrically connected to the power source, and a current flows through the HIFU transducer and the piezoelectric linear motor of the cartridge connected to the circuit, the HIFU transducer and the piezoelectric linear motor are driven.

In this case, a carbon shaft 201 of the piezoelectric linear motor 121 is a conductor which is connected to a silver electrode 200a of a piezoelectric actuator and through which an applied current flows. In addition, a coated silver electrode 21b of a lower portion of a piezoelectric actuator 20 in the transducer 122 is generally connected to a ground terminal of the power source.

However, in the cartridge according to the present invention, since the transducer is coupled to the carbon shaft of the piezoelectric linear motor, and the transducer and the carbon shaft are in contact with water in the cartridge, when a voltage is applied to the carbon shaft 201 of the piezoelectric linear motor, a voltage is applied to the coated silver electrode 21b, which is the ground terminal, on the lower portion of the piezoelectric actuator 20 in the transducer 122 due to the water, and an electrolysis phenomenon of the water occurs due to the applied voltage, and thus a phenomenon occurs in which the lower silver electrode 21b is delaminated from the piezoelectric actuator 20 of the transducer 122.

In other words, electrolysis of water occurs according to Reaction Formula 1 below.

$$2H_2O \rightarrow O_2 + 4H^+ + 4e^-, E^0 = 1.23 \text{ V} \qquad \text{[Reaction Formula 1]}$$

Figure 17A:
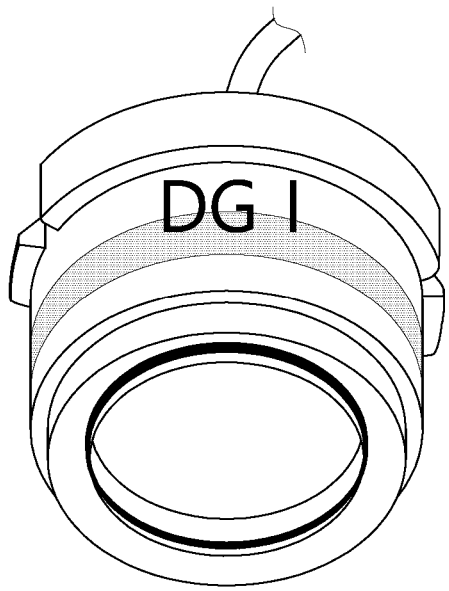
FIGS. 17A and 17B are views illustrating a transducer and a change of a piezoelectric element of the transducer according to wiring of wires of a piezoelectric linear motor in the HIFU device according to one embodiment of the present invention (FIG. 17A is a view illustrating a general transducer and FIG. 17B is a view illustrating a form in which an electrode thin film of the transducer is delaminated due to incorrect wiring)
Figure 17B:
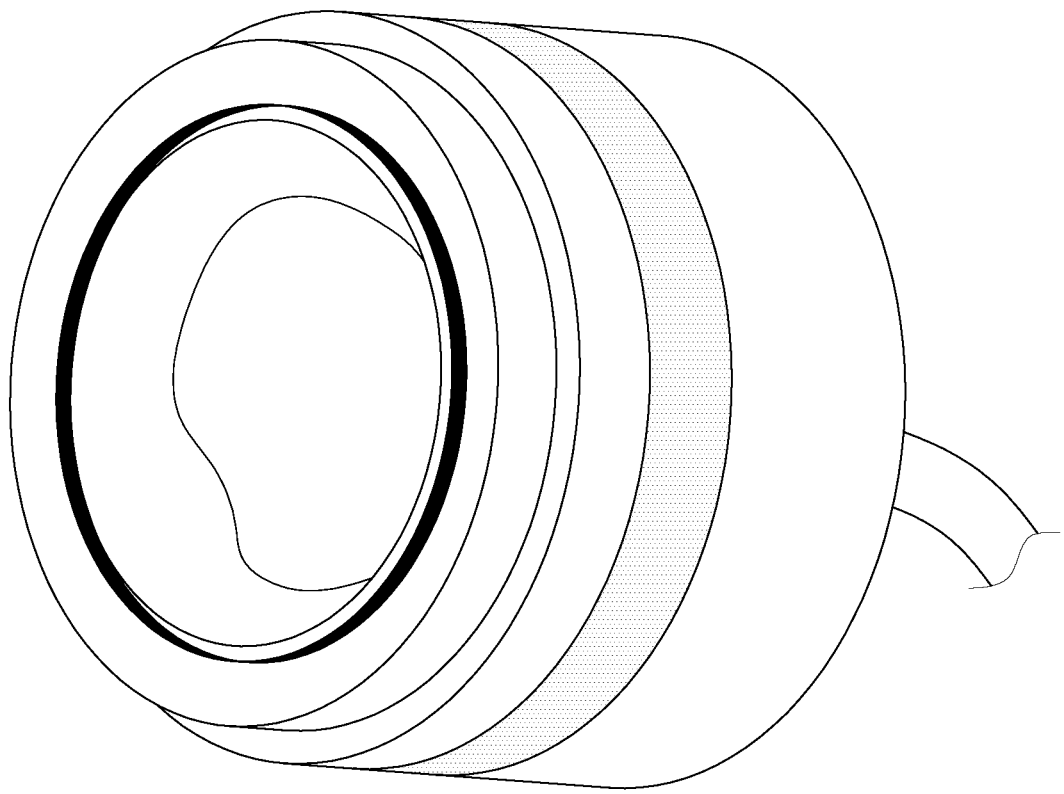

As shown in Reaction Formula 1, since an electromotive force is 1.23 V when water is electrolyzed, when a voltage of 1.23 V or more is applied, electrolysis occurs. Protons generated through the electrolysis diffuse to an interface between Ag and the piezoelectric actuator, meet electrons, and are reduced to hydrogen gas. A phenomenon occurs in which the silver electrode 21b applied on a lower end portion in the piezoelectric actuator 20 of the transducer 122 is inflated and delaminated due to the hydrogen gas, and thus ultrasound is not generated any more (see FIG. 17B).

Accordingly, in the HIFU device according to the present invention, a method of wiring the transducer in the cartridge and the piezoelectric linear motor to an external circuit is very important.

Figure 18:
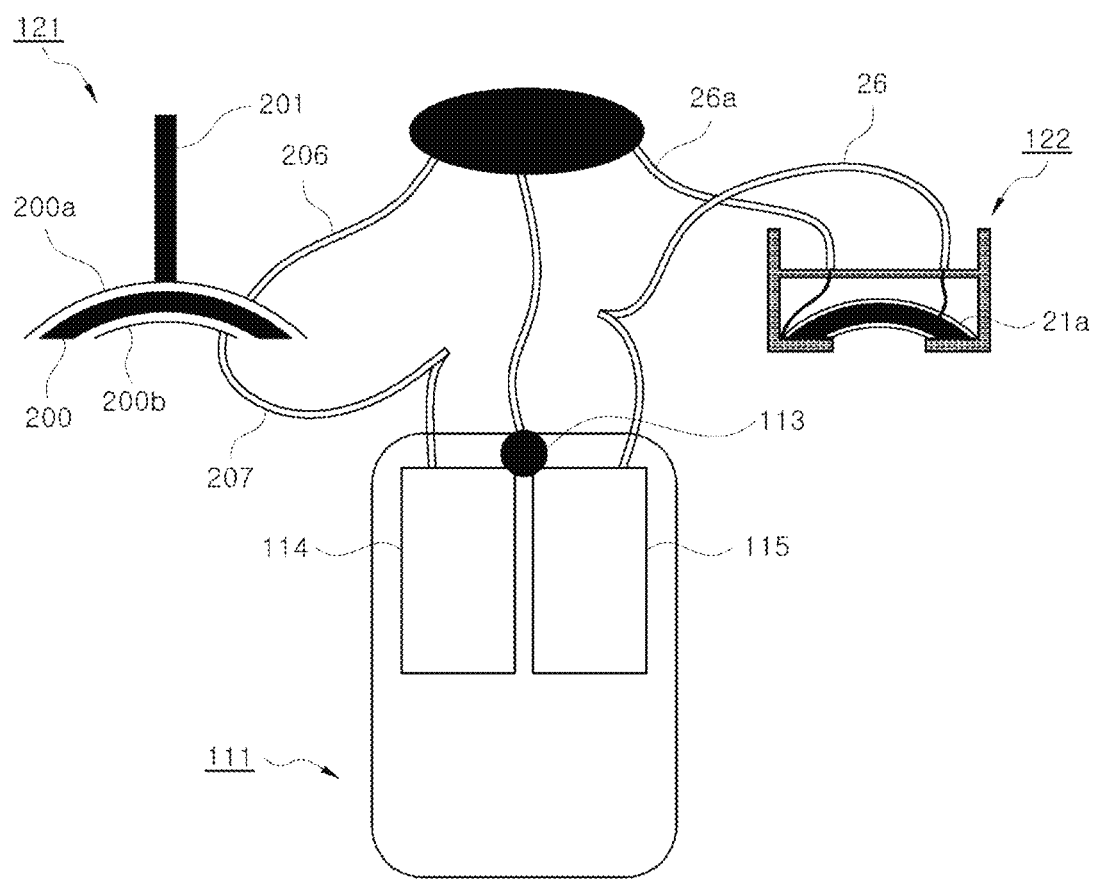
FIG. 18 is a view illustrating a form in which wires of the transducer in the cartridge and the piezoelectric linear motor in the HIFU device according to one embodiment of the present invention are wired to an external circuit.
Figure 19A:
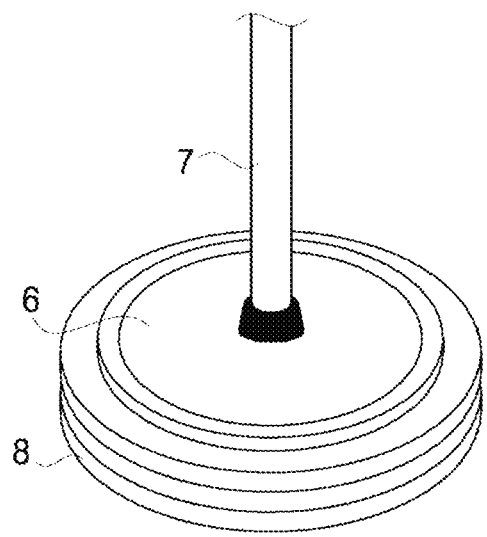
FIGS. 19 and 20 are views illustrating a conventional dome type piezoelectric linear motor.
Figure 19B:
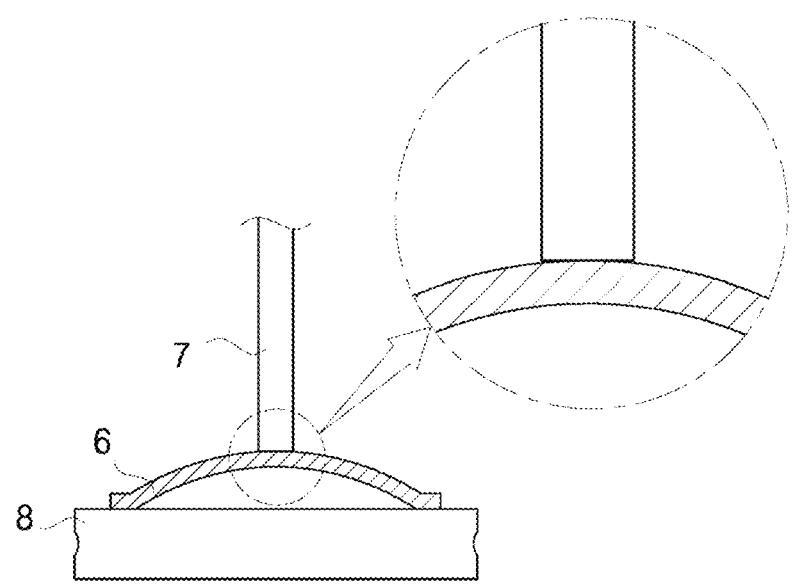
Figure 20A:
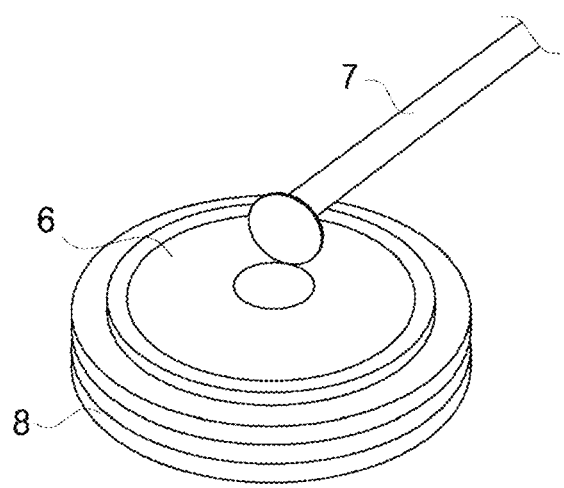
Figure 20B:
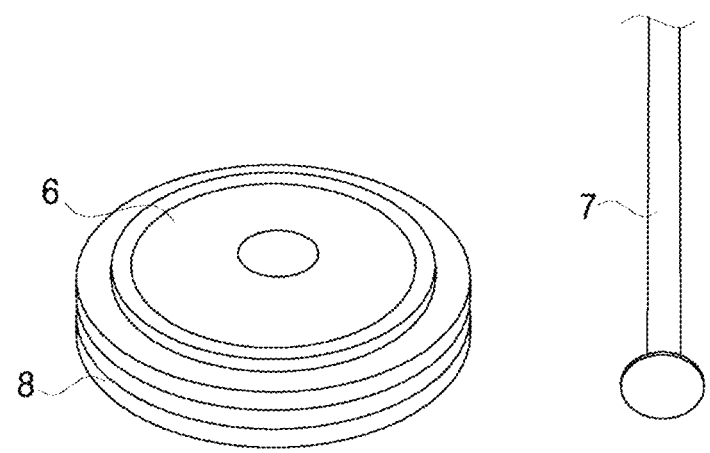

FIG. 18 is a view illustrating a form in which wires of the transducer in the cartridge and the piezoelectric linear motor in the HIFU device according to one embodiment of the present invention are wired to an external circuit.

As illustrated in FIG. 18, in the HIFU device according to the present invention, the method of wiring the wires of the transducer in the cartridge and the piezoelectric linear motor to the external circuit is that a wire 206 connected to the silver electrode 200a, which is applied on an upper portion of a piezoelectric actuator 200 and connected to the carbon shaft 201 of the piezoelectric linear motor, is connected to a common ground terminal 113 of the circuit 111, and a wire 1707 connected to the silver electrode 200b, which is applied onto a lower portion of the piezoelectric actuator 200 of the piezoelectric linear motor, is connected to a power terminal 114 of the circuit 111.

In addition, a wire 26a connected to the silver electrode 21b, which is applied onto the lower portion of the piezoelectric actuator in contact with water in the transducer 122, is connected to the common ground terminal 113, and the wire 26 connected to the silver electrode 21a, which is applied on the upper portion of the piezoelectric actuator of the transducer, is connected to a power terminal 115 of the circuit 111.

When the HIFU device is configured as described above, since the carbon shaft 201 in contact with the water in the cartridge and the ground terminals of both ultrasound focusing devices are common, a voltage is not fundamentally generated, and thus delamination of the silver electrode 21b of the lower end portion in contact with the water in the piezoelectric element of the transducer can be fundamentally prevented.

The present invention relates to the piezoelectric linear motor using a dome type piezoelectric actuator and provides the piezoelectric linear motor in which the dome type piezoelectric actuator is stably coupled to a moving shaft. The moving shaft is coupled to a peak portion of the dome type piezoelectric actuator such that a longitudinal direction of the moving shaft intersects a tangential direction of a peak of the piezoelectric actuator. That is, an end portion of the moving shaft is coupled to the peak of the piezoelectric actuator. In order to firmly couple the piezoelectric actuator to the moving shaft, a protrusion is formed on the peak portion of the piezoelectric actuator. A planar cross section of the protrusion may have a circular or polygonal shape, and a surface of the protrusion may be a flat surface. The moving shaft may be in direct contact with and coupled to the protrusion of the peak portion or may also be in indirect contact with the protrusion through a coupler. The coupler is provided with a first groove into which the protrusion of the dome type actuator is inserted and a second groove into which the moving shaft is inserted. The first groove and the second groove are disposed to be coaxial with each other, and the first groove communicates with the second groove, or the first groove does not communicate with the second groove, that is, in a blocked state therebetween. In a case in which the first groove and the second groove do not communicate with each other and have bottom surfaces, the bottom surfaces may be flat surfaces. After the protrusion of the dome type actuator is inserted into the first groove of the coupler and the moving shaft is inserted into the second groove, an epoxy may be used as a coupling material. The epoxy may preferably include a metal powder.

Hereinafter, the piezoelectric linear motor according to the exemplary embodiment of the present invention will be described in detail with reference the drawings.

Figure 21:
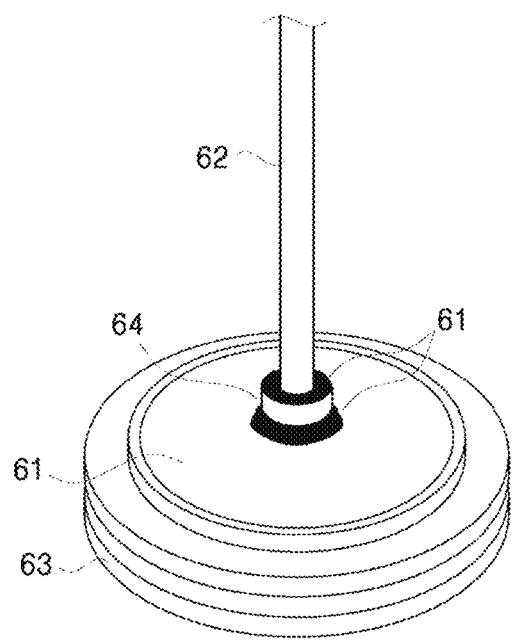
FIG. 21 is a view illustrating an exterior of the piezoelectric linear motor according to an exemplary embodiment of the present invention.
Figure 22:
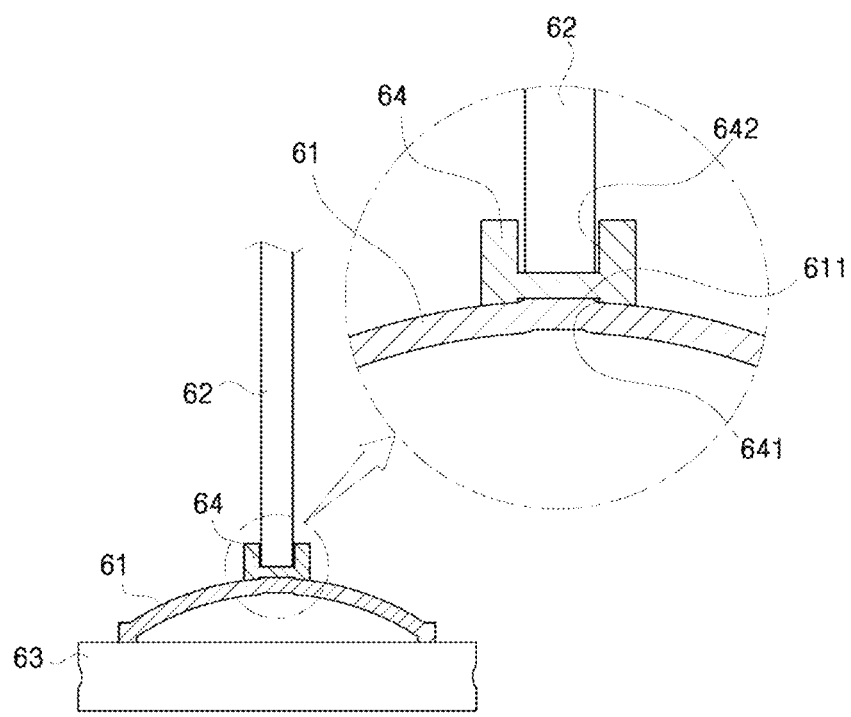
FIG. 22 is a cross-sectional view of FIG. 21.
Figure 23A:
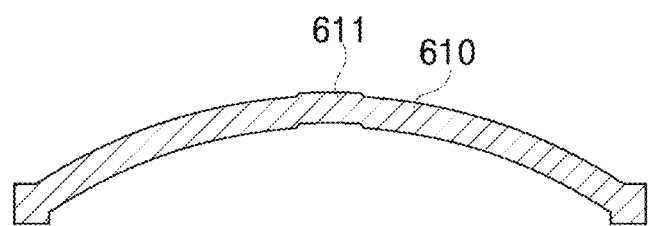
FIGS. 23A, 23B, and 23C are views illustrating a dome type piezoelectric actuator used in the piezoelectric linear motor of FIG. 21.
Figure 23B:
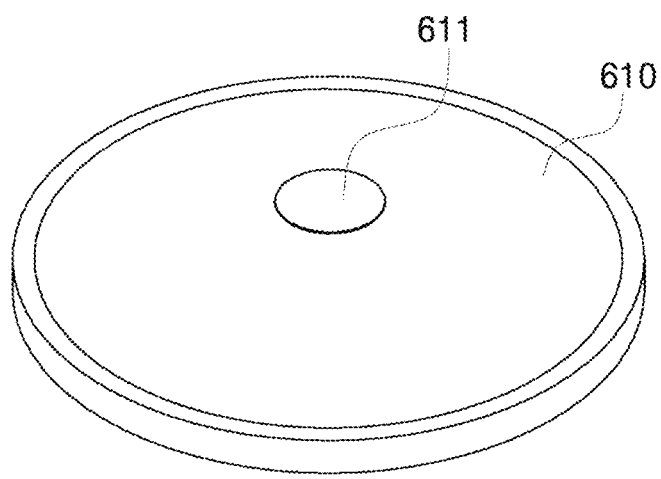
Figure 23C:
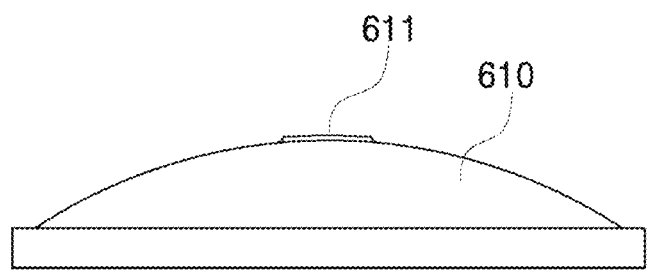
Figure 24:
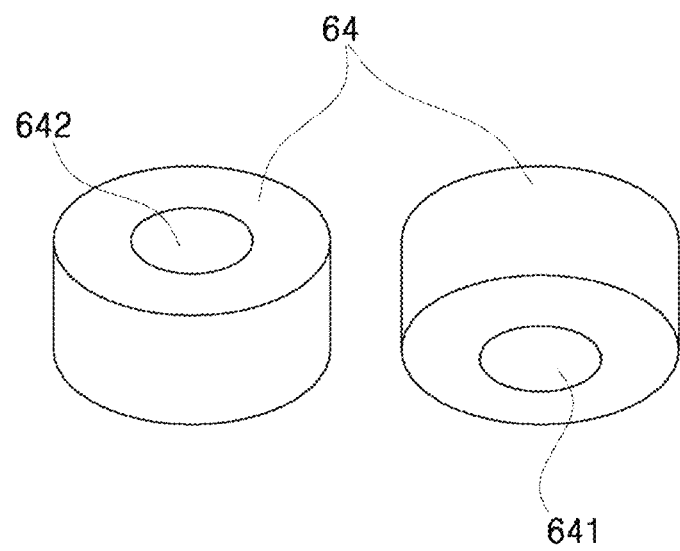
FIG. 24 is a view illustrating a coupler used in the piezoelectric linear motor of FIG. 21.

FIG. 21 is a view illustrating an exterior of a piezoelectric linear motor according to an exemplary embodiment of the present invention. FIG. 22 is a cross-sectional view of FIG. 21. FIGS. 23A, 23B, and 23C are views illustrating a dome type piezoelectric actuator used in the piezoelectric linear motor of FIG. 21, wherein FIG. 23A is a cross-sectional view illustrating the dome type piezoelectric actuator, FIG. 23B is a perspective view illustrating the dome type piezoelectric actuator, and FIG. 23C is a front view illustrating the dome type piezoelectric actuator. FIG. 24 is a view illustrating a coupler used in the piezoelectric linear motor of FIG. 21.

The piezoelectric linear motor according to the exemplary embodiment of the present invention includes a dome type piezoelectric actuator 61, a moving shaft 62 coupled to the piezoelectric actuator 61, and a moving member (not shown) mounted on the moving shaft 62, and a protrusion 611 formed on a peak of the dome type piezoelectric actuator 61. The dome type piezoelectric actuator 61 is formed of a ceramic material, and when power is applied thereto, displacement occurs due to deformation. The moving shaft 62 is coupled to the piezoelectric actuator 61 to operate in conjunction with the displacement of the piezoelectric actuator 61. The moving member is mounted thereon to linearly operate due to friction with the moving shaft 62. The drawing symbol "63" denotes a support ceramic.

In the piezoelectric linear motor according to the present invention, the moving shaft 62 may be in direct or indirect contact with and be coupled to a protrusion 611 formed on the peak of the dome type piezoelectric actuator 61. In the piezoelectric linear motor according to the present invention, when the moving shaft 62 is coupled to the peak of the dome type piezoelectric actuator 61, a lower surface (flat surface) of an end portion of the moving shaft 62 is not in contact with a curved surface of the dome type piezoelectric actuator 61. Accordingly, the protrusion 611 having a flat upper surface is formed so that the flat surfaces are in contact with each other. The upper surface of the protrusion 611 is parallel to a bottom surface of the piezoelectric actuator 61 and is parallel to the lower surface of the end portion of the moving shaft 62. In addition, a planar cross section of the protrusion 611 may have a circular or polygonal shape.

In the exemplary embodiment, the piezoelectric linear motor may include a coupler 64, and the moving shaft 62 is coupled to the piezoelectric actuator 61 through the coupler 64.

The coupler 64 includes a first groove 641 and a second groove 642 into which the protrusion 611 of the piezoelectric actuator 61 and the moving shaft 62 are inserted from both sides of the coupler 64. Bottom surfaces of the first groove 641 and the second groove 642 may be flat surfaces.

As shown in FIG. 22, when the coupler 64 is placed on a surface of the dome type piezoelectric actuator 61, the coupler 64 is placed such that the protrusion 611 of the dome type piezoelectric actuator 61 is inserted into the first groove 641 of the coupler 64.

The moving shaft 62 is inserted into the second groove 642 formed in an upper portion of the coupler 64. The moving shaft 62 may be, for example, a carbon rod.

A conductive epoxy may be used to couple the piezoelectric actuator 61 to the coupler 64 and to couple the coupler 64 to the moving shaft 62. The conductive epoxy may include a metal powder.

The coupler 64 may have an electrical conductivity of $10^5$ S/m or more at room temperature. A material of the coupler may be aluminum, copper, titanium, nickel, tungsten, stainless steel, or an alloy thereof.

The first groove 641 and the second groove 642 formed in the coupler 64 may be coaxially disposed. In addition, the first groove 641 may or may not communicate with the second groove 642. As described above, in the exemplary embodiment in which the first groove 641 does not communicate with the second groove 642, the bottom surface of the first groove 641 and the bottom surface of the second groove 642 may be the flat surfaces.

In addition, a difference between a curvature of a portion of the coupler 64 in contact with a curved surface of the piezoelectric actuator 61 and a curvature of the piezoelectric actuator 61 may be less than 10%. The portion of the coupler 64 in contact with the piezoelectric actuator 61 may have a curvature ranging from 2 to 20 mm.

Figure 25:
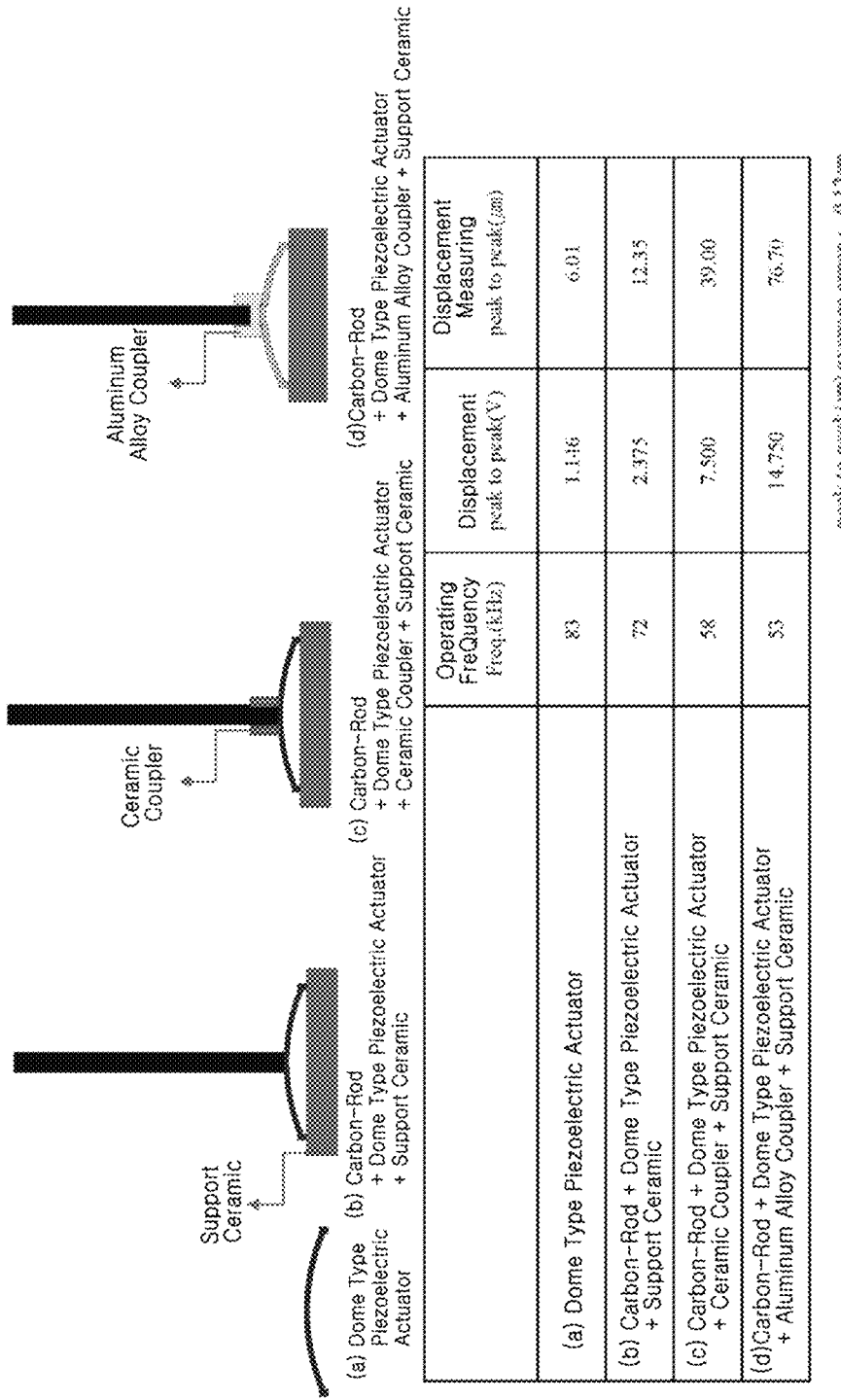
FIG. 25 is a view illustrating a displacement comparison between the piezoelectric linear motor according to the present invention and the conventional piezoelectric linear motor.
Figure 26A:
FIGS. 26A, 26B, 26C, and 26D are graphs showing vibration displacement of the piezoelectric linear motors of FIG. 25.
Figure 26A:
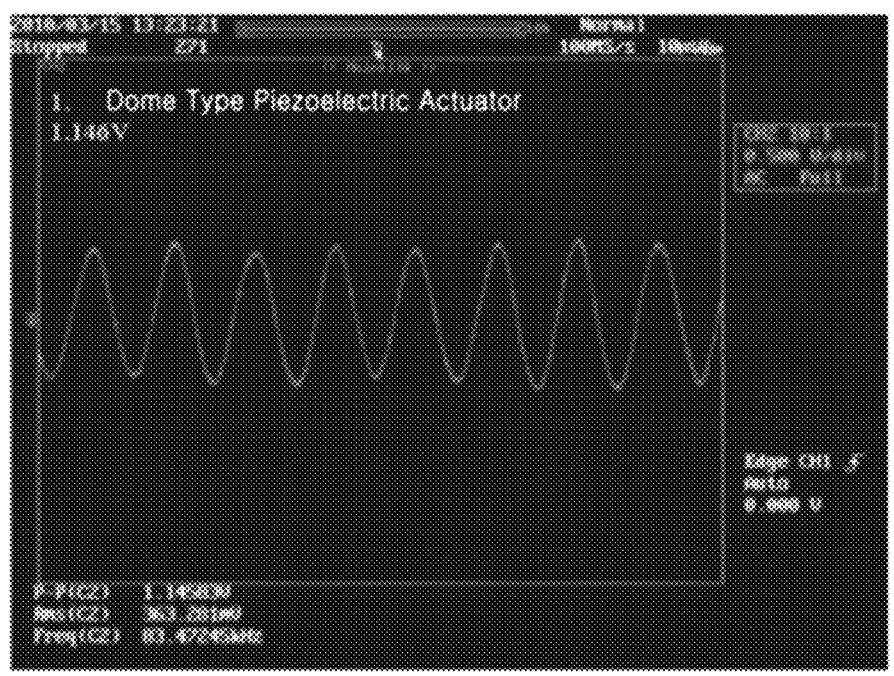
Figure 26B:
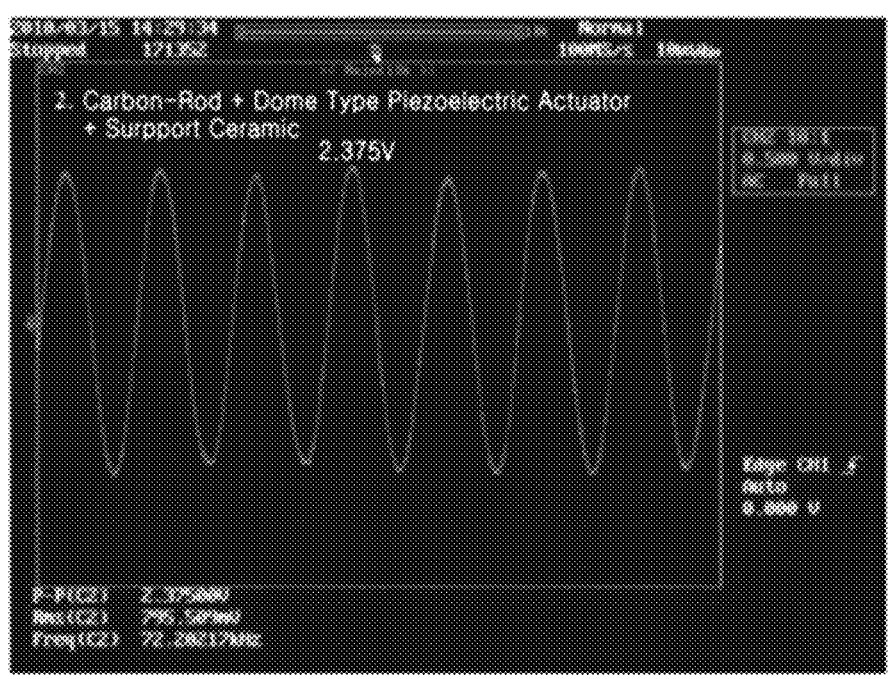
Figure 26C:
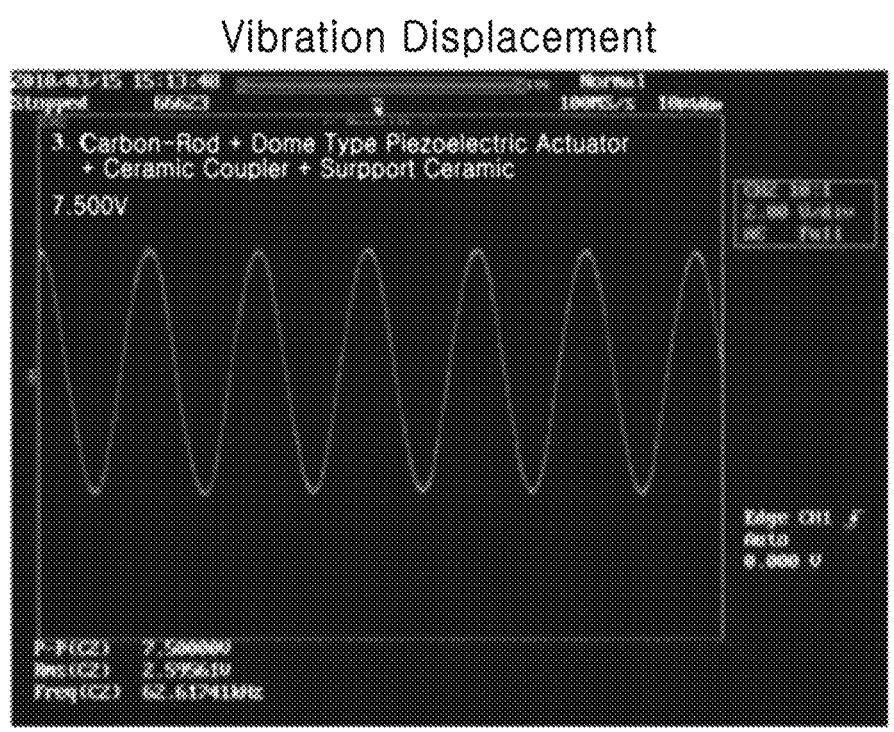
Figure 26D:
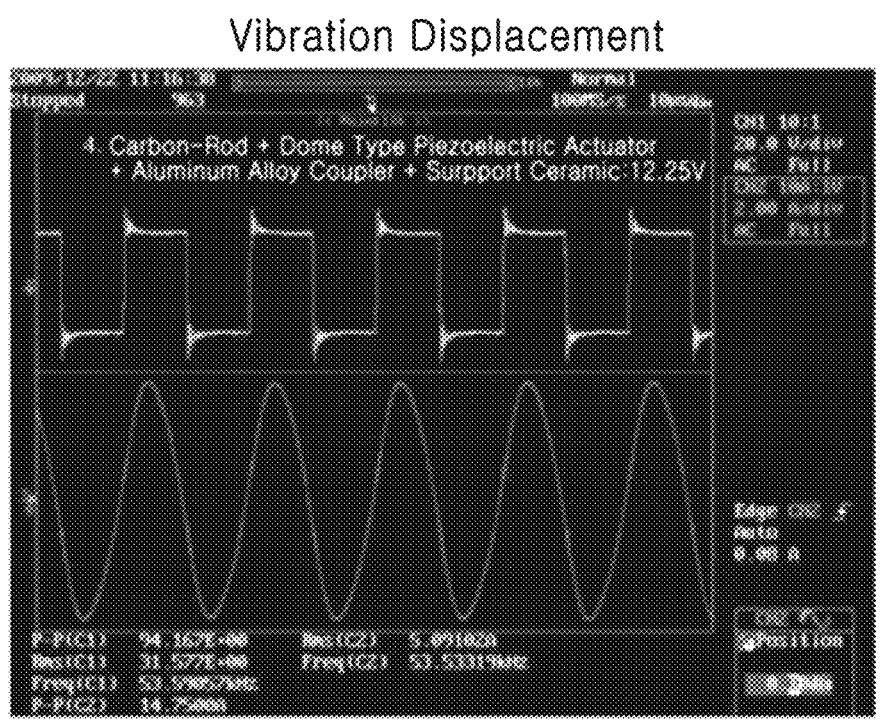

In another example of the coupler, a third ceramic coupler in FIG. 25 having a cylindrical form may be used. The cylindrical ceramic coupler includes a hole vertically passing through the coupler. A moving shaft 62 may be inserted into a hole and be in contact with a surface of a protrusion

611. A density of the cylindrical ceramic coupler may be between a density of a piezoelectric actuator and a density of a moving shaft.

FIG. 25 is a view illustrating a displacement comparison between the piezoelectric linear motor according to the present invention and the conventional piezoelectric linear motor, FIG. 25A relates to the dome type piezoelectric actuator, FIG. 25B relates to the carbon rod, the dome type piezoelectric actuator, and the support ceramic, FIG. 25C relates to the carbon rod, the dome type piezoelectric actuator, the cylindrical ceramic coupler, and the support ceramic, and FIG. 25D relates to the carbon rod, the dome type piezoelectric actuator, the aluminum alloy coupler, and the support ceramic.

FIGS. 26A, 26B, 26C, and 26D are graphs showing vibration displacement of the piezoelectric linear motors of FIG. 25.

Measuring equipment was MTI-2100 FOTONIC SENSOR (manufactured by MTI instruments) which is a non-contact precision displacement measuring equipment, and a voltage of 30 Vrms was applied to all linear piezoelectric motors to measure displacement. A wave form of the applied voltage was a square wave form as shown in an upper portion of FIG. 26D. A 2032RX probe was used as a sensor for measuring. A oscilloscope was connected thereto to read measured vibration displacement as a voltage, vibration displacement was measured within a range of Vp-p, and measured values were shown in a table of FIG. 25. Meanwhile, results of converting output vibration voltages into displacement using an equation provided from the manufacturer of the displacement measuring equipment were shown in the last line of FIG. 25. The equation used was Equation 1 below.

$$\text{Vibration displacement } (\mu m) = 0.0052 \times 1000 \times Vp\text{-}p \quad (1)$$

In the cartridge for a HIFU device according to the present invention, since a transducer module is coupled to a piezoelectric linear motor capable of being driven in water and is embedded in the cartridge, heat generated when a conventional step motor is driven is fundamentally removed, and thus an additional cooling fan is not needed. In addition, since the piezoelectric linear motor is driven even with a power consumption of one watt or less, ultra-low power consumption can be realized. In addition, since the piezoelectric linear motor may constantly transfer ultrasound less than 1 mm which is effective in skin regeneration, ultra-precise transfer can be performed, and thus an effective procedure can be performed. In addition, since the piezoelectric linear motor and the transducer module are detachable, replacement thereof is easy. The cartridge according to the present invention can be effectively used in a high intensity focused ultrasound (HIFU) device due to the above advantages.

In addition, according to the present invention, the piezoelectric linear motor is provided which has a firm and stable connection structure between a dome type piezoelectric actuator and a moving shaft. Since a protrusion having a flat upper surface for connecting the moving shaft is formed on a peak of the dome type piezoelectric actuator, the protrusion of the dome type piezoelectric actuator can be coupled to the moving shaft through the flat surfaces. Particularly, since a coupler including grooves into which the protrusion and the moving shaft are inserted is used, high coupling stability can be secured.

While the example embodiments of the present invention and their advantages have been described in detail, it should be understood that various changes, substitutions and alterations may be made herein without departing from the scope of the invention.

What is claimed is:

1. A cartridge for a high intensity focused ultrasound device, comprising:
   a cartridge housing in which a sound transmission medium is stored and a transmission window sealed by an ultrasound transmission film is formed in a lower portion thereof;
   a transducer embedded in the cartridge housing, controlled by a main body, and configured to generate a high intensity focused ultrasound; and
   a piezoelectric linear motor embedded in the cartridge housing, controlled by the main body, and configured to move the transducer,
   wherein the piezoelectric linear motor includes:
      a dome type piezoelectric actuator;
      a transfer shaft that is disposed at and perpendicular to a center of a convex surface of the piezoelectric actuator and formed to have a predetermined length;
      a connector connecting the piezoelectric actuator and the transfer shaft;
      silver electrodes applied on an upper surface and a lower surface of the piezoelectric actuator; and
      wires connected to the silver electrodes,
      wherein the piezoelectric actuator is covered by a housing for waterproofing, and a transfer member is coupled to the transfer shaft so that the transfer member is moveable along the transfer shaft.

2. The cartridge of claim 1, wherein the transducer includes:
   a transducer housing;
   a dome type piezoelectric actuator installed on a lower end portion of the transducer housing and configured to generate a high intensity focused ultrasound;
   silver electrodes applied on an upper surface and a lower surface of the piezoelectric actuator; and
   wires connected to the silver electrodes,
   wherein the transducer is embedded in a support to be transferred.

3. The cartridge of claim 1, wherein the transducer and the piezoelectric linear motor are detachably coupled to the cartridge housing using a bolt or a coupling method.

4. The cartridge of claim 1, wherein the transducer is coupled and integrated with the transfer shaft of the piezoelectric linear motor using a support coupled to the transfer member.

5. The cartridge of claim 4, wherein the transducer is integrally coupled to the piezoelectric linear motor by:
   inserting the transfer member into an inner space of the support of the transducer; and
   passing the transfer shaft of the piezoelectric linear motor through the transfer member and a hole of the support.

6. A high intensity focused ultrasound device comprising:
   the cartridge including the transducer and the piezoelectric linear motor of claim 1; and
   a main body coupled to the cartridge,
   wherein the main body includes a circuit and a power source, and
   the circuit is connected to the transducer and the piezoelectric linear motor of the cartridge through wires.

7. The high intensity focused ultrasound device of claim 6, wherein a method of wiring the transducer and the piezoelectric linear motor to the circuit incudes:
   connecting the wire, which is formed in an upper portion of the dome type piezoelectric actuator of the piezoelectric linear motor connected to the transfer shaft and is in contact with a medium in the cartridge, and the wire formed in a lower portion of a piezoelectric actuator of the transducer to a common ground terminal of the circuit; and connecting the remaining wire to a power terminal of the circuit.

\* \* \* \* \*